(12) United States Patent
Ebert et al.

(10) Patent No.: US 7,767,807 B2
(45) Date of Patent: Aug. 3, 2010

(54) USE OF PHTHALOCYANINES AS MARKING SUBSTANCES FOR LIQUIDS

(75) Inventors: Sophia Ebert, Mannheim (DE); Thomas Gessner, Heidelberg (DE); Ruediger Sens, Ludwigshafen (DE); Christos Vamvakaris, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 784 days.

(21) Appl. No.: 10/586,446

(22) PCT Filed: Jan. 14, 2005

(86) PCT No.: PCT/EP2005/000307

§ 371 (c)(1),
(2), (4) Date: Jul. 18, 2006

(87) PCT Pub. No.: WO2005/070935

PCT Pub. Date: Aug. 4, 2005

(65) Prior Publication Data

US 2008/0227973 A1    Sep. 18, 2008

(30) Foreign Application Priority Data

Jan. 23, 2004  (DE) .................. 10 2004 003 791

(51) Int. Cl.
*C07B 47/00* (2006.01)
*C07D 487/22* (2006.01)
*C09D 11/00* (2006.01)

(52) U.S. Cl. ................................. 540/145; 106/31.27
(58) Field of Classification Search ................ 540/145; 106/31.27

See application file for complete search history.

(56) References Cited

U.S. PATENT DOCUMENTS 4,451,398 A * 5/1984 Patsch et al. ................ 534/752

FOREIGN PATENT DOCUMENTS

| DE | 1 239 270 | | 4/1967 |
|---|---|---|---|
| DE | 1239270 | * | 4/1967 |
| EP | 0 034 725 | | 9/1981 |
| GB | 2 328 184 | | 2/1999 |
| JP | 2001-201850 | | 7/2001 |
| JP | 2001201850 | * | 7/2001 |
| WO | 94/02570 | | 2/1994 |
| WO | 98/52950 | | 11/1998 |

* cited by examiner

*Primary Examiner*—James O. Wilson
*Assistant Examiner*—Paul V. Ward
(74) *Attorney, Agent, or Firm*—Oblon, Spivak, McClelland, Maier & Neustadt, L.L.P.

(57) ABSTRACT

The present invention relates to the use of specific phthalocyanines which bear substituents on the basic phthalocyanine structure bonded via methylene groups as markers for liquids, especially mineral oils, to liquids, especially mineral oils which comprise at least one such phthalocyanine as a marker, and also to novel specific phthalocyanines which bear substituents on the basic phthalocyanine structure bonded via methylene groups.

17 Claims, No Drawings

USE OF PHTHALOCYANINES AS MARKING SUBSTANCES FOR LIQUIDS

The present invention relates to the use of specific phthalocyanines which bear substituents on the basic phthalocyanine structure bonded via methylene groups as markers for liquids, especially mineral oils, to liquids, especially mineral oils, which comprise at least one such phthalocyanine as a marker, and also to novel specific phthalocyanines which bear substituents on the basic phthalocyanine structure bonded via methylene groups.

The document EP 0 034 725 A2 describes, inter alia, phthalocyanines containing imidazolylmethyl groups and their use as wetfast cellulose dyes.

Flocculation-resistant and solvent-resistant phthalocyanine pigment mixtures which comprise phthalocyaninemethylenamines are disclosed by DE-B1 239 270.

The document GB 2 328 184 A describes pigment compositions which have qualities including outstanding rheological properties and which result from additization with pigment derivatives which have methylene-bonded cyclic radicals as substituents.

However, the use of the correspondingly substituted phthalocyanines as markers for liquids, especially mineral oils, is not disclosed by any of the aforementioned documents.

In addition to other compounds, the document WO 94/02570 A1 also proposes phthalocyanine derivatives as markers for liquids, especially mineral oils.

In addition, the document WO 98/52950 A1 proposes, as markers for liquids, especially mineral oils, phthalocyanines which contain, as substituents, five- or six-membered saturated nitrogen-containing heterocyclic radicals which are bonded to the basic phthalocyanine structure via a ring nitrogen atom.

In practice, it has been found that, especially in mineral oils with the additives typically present therein, the phthalocyanine markers disclosed in the documents WO 94/02570 A1 and WO 98/52950 A1 often do not have the desired long-term stability. The action of said additives results in a change in the characteristics (for example extinction) of the markers within a very short time.

It is thus an object of the present invention to provide phthalocyanines which feature not only good solubility, but also very good long-term stability in the liquids to be marked, especially mineral oils.

Accordingly, the use has been found of phthalocyanines of the formula I

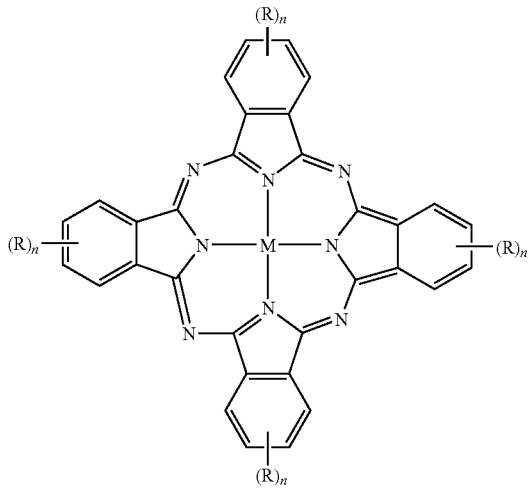

(I)

as markers for liquids, where, in formula I,

M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are each identical or different moieties selected from the group consisting of —CH$_2$—N(—X$^1$—R$^1$)(—X$^2$—R$^2$) and —CH$_2$-Het, X$^1$, X$^2$ are each independently a carbonyl group or a chemical single bond, R$^1$ is C$_1$-C$_{20}$-alkyl which is optionally interrupted by from 1 to 4 oxygen atoms in ether function, C$_5$-C$_7$-cycloalkyl which is optionally substituted by one or more C$_1$-C$_{20}$-alkyl groups which are optionally interrupted by from 1 to 4 oxygen atoms in ether function, saturated heterocyclic five- or six-membered radical which is optionally substituted by one or more C$_1$-C$_{20}$-alkyl groups which are optionally interrupted by from 1 to 4 oxygen atoms in ether function, C$_6$-C$_{10}$-aryl which is optionally substituted by one or more halogen, cyano, nitro, hydroxyl, amino, C$_1$-C$_{20}$-alkyl which is optionally substituted by from 1 to 4 oxygen atoms in ether function, C$_1$-C$_{20}$-alkoxy, C$_1$-C$_{20}$-alkylamino or C$_1$-C$_{20}$-dialkylamino, heteroaryl having from 3 to 12 carbon atoms which is optionally substituted by one or more C$_1$-C$_{20}$-alkyl which is optionally interrupted by from 1 to 4 oxygen atoms in ether function, C$_1$-C$_{20}$-alkoxy, C$_1$-C$_{20}$-alkylamino or C$_1$-C$_{20}$-dialkylamino, C$_6$-C$_{10}$-aryl-C$_1$-C$_4$-alkyl which is optionally substituted in the aryl radical by one or more halogen, cyano, nitro, hydroxyl, amino, C$_1$-C$_{20}$-alkyl which is optionally interrupted by from 1 to 4 oxygen atoms in ether function, C$_1$-C$_{20}$-alkoxy, C$_1$-C$_{20}$-alkylamino or C$_1$-C$_{20}$-dialkylamino, or heteroaryl-C$_1$-C$_4$-alkyl having from 3 to 12 carbon atoms in the heteroaryl radical, the latter optionally being substituted by one or more C$_1$-C$_{20}$-alkyl which is optionally interrupted by from 1 to 4 oxygen atoms in ether function, C$_1$-C$_{20}$-alkoxy, C$_1$-C$_{20}$-alkylamino or C$_1$-C$_{20}$-dialkylamino, R$^2$ is hydrogen or, independently of R$^1$, as defined for R$^1$, and, in the case that X$^2$ is a carbonyl group, R$^2$ is not defined as hydrogen, Het is a saturated heterocyclic five-, six- or seven-membered radical which is optionally interrupted by one or more C$_1$-C$_{20}$-alkyl groups which are optionally interrupted by from 1 to 4 oxygen atoms in ether function, and in which one CH$_2$ group is optionally replaced by a carbonyl group, or heteroaryl having from 3 to 12 carbon atoms which is optionally substituted by one or more C$_1$-C$_{20}$-alkyl groups which are optionally interrupted by from 1 to 4 oxygen atoms in ether function, the saturated heterocyclic radical or the heteroaryl being bonded to the CH$_2$ group of the —CH$_2$-Het moiety either via a suitable heteroatom or a carbon atom, and n is in each case independently a value of 0, 1, 2, 3 or 4, with the proviso that the sum of the four values of n is at least 1.

C$_1$-C$_{20}$-Alkyl which is optionally interrupted by from 1 to 4 oxygen atoms in ether function includes, for example, methyl, ethyl, propyl, isopropyl, butyl, isobutyl, sec-butyl, tert-butyl, pentyl, isopentyl, neopentyl, tert-pentyl, hexyl, 2-methylpentyl, heptyl, hept-3-yl, octyl, 2-ethylhexyl, isooctyl, nonyl, isononyl, decyl, isodecyl, undecyl, dodecyl, tridecyl, 3,5,5,7-tetramethylnonyl, isotridecyl (the above terms isooctyl, isononyl, isodecyl and isotridecyl are trivial terms and stem from the alcohols obtained by the oxo process—on this subject, cf. Ullmanns Encyklopädie der technischen Chemie, 4th edition, Volume 7, pages 215 to 217, and Volume 11, pages 435 and 436), tetradecyl, pentadecyl, hexadecyl, heptadecyl, octadecyl, nonadecyl, eicosyl, methoxymethyl, 2-ethylhexoxymethyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 2- or 4-butoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 4,8-dioxadecyl, 3,6,8-trioxadecyl, 3,6,9-trioxaundecyl, 3,6,9,12-tetraoxamidecyl or 3,6,9,12-tetraoxatetradecyl.

Useful $C_5$-$C_7$-cycloalkyl radicals include cyclopentyl, cyclohexyl and cycloheptyl. These cycloalkyls are optionally also substituted by one or more, in particular up to three, $C_1$-$C_{20}$-alkyl groups, the latter also optionally being interrupted by from 1 to 4 oxygen atoms in ether function. Examples of such $C_1$-$C_{20}$-alkyl groups also optionally interrupted by oxygen atoms have already been listed above.

Saturated heterocyclic five- or six-membered radicals which are optionally substituted by one or more $C_1$-$C_{20}$-alkyl groups which are optionally interrupted by from 1 to 4 oxygen atoms in ether function are derived, for example, from pyrrolidine, 2- or 3-methylpyrrolidine, 2,4-dimethyl-3-ethylpyrrolidine, pyrazolidine, 2-, 3-, 4- or 5-methylpyrazolidine, imidazolidine, 2-, 3-, 4- or 5-methylimidazolidine, oxazolidine, 2-, 4- or 5-methyloxazolidine, isoxazolidine, 3-, 4- or 5-methylisoxazolidine, piperidine, 2-, 3-, 4-methyl- or -ethylpiperidine, 2,6-dimethylpiperidine, piperazine, 4-($C_1$-$C_4$-alkyl)-piperazine, such as 4-methyl- or 4-ethylpiperazine, morpholine, thiomorpholine or thiomorpholine S,S-dioxide. The terminology "are derived" is to be interpreted in this context to the effect that the radicals derived are obtained from the heterocycles mentioned above by way of example by abstraction of a carbon atom or, where present, heteroatom-bound hydrogen atom. For example, the piperidin-1-yl and piperidinyl-2-yl radicals are derived from piperidine by abstraction of the nitrogen-bonded hydrogen atom or of a hydrogen atom or of a hydrogen atom carbon-bonded in the 2-position.

When $R^1$ and $R^2$ correspond to an optionally substituted saturated heterocyclic five- or six-membered radical and both $X^1$ and $X^2$ are defined as a chemical single bond, the radical is bonded to the nitrogen atom of the —$CH_2$—N(—$X^1$—$R^1$)(—$X^2$—$R^2$) moiety via a carbon atom of the heterocyclic five- or six-membered radical.

$C_6$-$C_{10}$-Aryls include in particular phenyl and naphthyl. These are optionally substituted by one or more halogen, for instance fluorine, chlorine or bromine, cyano, nitro, hydroxyl, amino, $C_1$-$C_{20}$-alkyl which is optionally interrupted by from 1 to 4 oxygen atoms in ether function, $C_1$-$C_{20}$-alkoxy, $C_1$-$C_{20}$-alkylamino or $C_1$-$C_{20}$-dialkylamino. Corresponding $C_1$-$C_{20}$-alkyl radicals which are optionally interrupted by from 1 to 4 oxygen atoms in ether function, or $C_1$-$C_{20}$-alkyl radicals which are present in the $C_1$-$C_{20}$-alkoxy, $C_1$-$C_{20}$-alkylamino or $C_1$-$C_{20}$-dialkylamino groups have already been listed above by way of example.

Heteroaryl radicals having from 3 to 12 carbon atoms which are optionally interrupted by one or more $C_1$-$C_{20}$-alkyl which is optionally interrupted by from 1 to 4 oxygen atoms in ether function, $C_1$-$C_{20}$-alkoxy, $C_1$-$C_{20}$-alkylamino or $C_1$-$C_{20}$-dialkylamino are derived, for example, from pyrrole, furan, thiophene, pyrazole, isoxazole, isothiazole, imidazole, 1H-1,2,3-triazole, 1H-1,2,4-triazole, pyridine, pyrazine, pyridazine, 1H-azepine, 2H-azepine, oxazole, thiazole, 1,2,3-, 1,2,4- or 1,3,4-oxadiazole, 1,2,3-, 1,2,4- or 1,3,4-thiadiazole and also, if appropriate, the benzo- or dibenzofused rings, for example quinoline, isoquinoline, indole, benzo[b]furan (coumarone), benzo[b]thiophene (thionaphthene), carbazole, dibenzofuran, dibenzothiophene, 1H-indazole, indoxazole, benzo[d]isothiazole, anthranil, benzimidazole, benzoxazole, benzothiazole, cinnoline, phthalazine, quinazoline, quinoxaline or phenazine. $C_1$-$C_{20}$-Alkyl substituents which are optionally interrupted by from 1 to 4 oxygen atoms in ether function have already been listed above by way of example.

When $R^1$ and $R^2$ correspond to optionally substituted heteroaryl and both $X^1$ and $X^2$ are defined as a chemical single bond, the radical is bonded to the nitrogen atom of the —$CH_2$—N(—$X^1$—$R^1$)(—$X^2$—$R^2$) moiety via a carbon atom of the heteroaryl.

$C_6$-$C_{10}$-Aryl-$C_1$-$C_4$-alkyls which are optionally substituted in the aryl radical by one or more halogen, cyano, nitro, hydroxyl, amino, $C_1$-$C_{20}$-alkyl which is optionally interrupted by from 1 to 4 oxygen atoms in ether function, $C_1$-$C_{20}$-alkoxy, $C_1$-$C_{20}$-alkylamino or $C_1$-$C_{20}$-dialkylamino include in particular benzyl, phenylethyl, 3-phenylpropyl and 4-phenylbutyl. Appropriate $C_1$-$C_{20}$-alkyl radicals which are optionally interrupted by from 1 to 4 oxygen atoms in the ether function or $C_1$-$C_{20}$-alkyl radicals which are present in the $C_1$-$C_{20}$-alkoxy, $C_1$-$C_{20}$-alkylamino or $C_1$-$C_{20}$-dialkylamino groups have already been listed above by way of example.

Heteroaryl-$C_1$-$C_4$-alkyls having from 3 to 12 carbon atoms in the heteroaryl radical, the latter optionally being substituted by one or more $C_1$-$C_{20}$-alkyl which is optionally interrupted by from 1 to 4 oxygen atoms in ether function, $C_1$-$C_{20}$-alkoxy, $C_1$-$C_{20}$-alkylamino or $C_1$-$C_{20}$-dialkylamino, are derived, for example, from the heteroaryl radicals already mentioned above which are bonded to the $C_1$-$C_4$-alkyl radicals either via a carbon atom or a heteroatom, suitable for bonding, of the heteroaryl. Appropriate $C_1$-$C_{20}$-alkyl radicals which are optionally interrupted by from 1 to 4 oxygen atoms in ether function or $C_1$-$C_{20}$-alkyl radicals which are present in the $C_1$-$C_{20}$-alkoxy, $C_1$-$C_{20}$-alkylamino or $C_1$-$C_{20}$-dialkylamino groups have already been listed above by way of example.

In addition to the optionally substituted saturated heterocyclic five- or six-membered radicals already mentioned by way of example, which are derived from the corresponding five- or six-membered heterocycles, possible radicals for the Het variable generally additionally include those seven-membered radicals which are derived from the corresponding seven-membered heterocycles. Examples of the latter include oxepane, thiepane and azepane. In addition, also possible are five-, six- or seven-membered radicals in which one $CH_2$ group has been replaced by a carbonyl group. The latter are in particular five-, six- or seven-membered lactone or lactam radicals.

In general, the saturated heterocyclic radical or the heteroaryl is bonded to the $CH_2$ group of the —$CH_2$-Het moiety either via a suitable heteroatom or a carbon atom.

In the case of the aforementioned lactams, the bonding to the $CH_2$ group of the —$CH_2$-Het moiety preferably takes place via the ring nitrogen atom.

Preference is given to using phthalocyanines of the formula I in which M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are each identical or different —CH$_2$-Het moieties, Het is a saturated heterocyclic five-, six- or seven-membered radical which is optionally substituted by one or more C$_1$-C$_{15}$-alkyl groups which are optionally interrupted by from 1 to 4 oxygen atoms in ether function, and in which one CH$_2$ group is optionally replaced by a carbonyl group, or heteroaryl having from 3 to 5 carbon atoms which is optionally substituted by one or more C$_1$-C$_{15}$-alkyl groups which are optionally interrupted by from 1 to 4 oxygen atoms in ether function.

Particular preference is given to using phthalocyanines of the formula I in which M is twice hydrogen, twice lithium, magnesium, zinc, copper, nickel, VO, TiO, AlCl, AlO-COCH$_3$, AlOCOCF$_3$, SiCl$_2$ or Si(OH)$_2$, R are each identical or different —CH$_2$-Het moieties and Het is a saturated heterocyclic five-, six- or seven-membered radical which is optionally substituted by one or more C$_1$-C$_4$-alkyl groups, and in which one CH$_2$ group is optionally replaced by a carbonyl group, or heteroaryl having from 3 to 5 carbon atoms which is optionally substituted by one or more C$_1$-C$_4$-alkyl groups.

Particularly advantageously, phthalocyanines of the formula I are used in which M is twice hydrogen, R are identical or different —CH$_2$-Het moieties, Het is a saturated nitrogen-containing five-, six- or seven-membered radical which is optionally substituted by one or more C$_1$-C$_4$-alkyl groups and in which the CH$_2$ group adjacent to the nitrogen atom is replaced by a carbonyl group or a nitrogen-containing heteroaryl having from 3 to 5 carbon atoms which is optionally substituted by one or more C$_1$-C$_4$-alkyl groups.

In all preferences recited above, the saturated heterocyclic radical or the heteroaryl in the phthalocyanines of the formula I is bonded to the CH$_2$ group of the —CH$_2$-Het moiety either via a suitable nitrogen atom or a carbon atom; in addition, the variable n in formula I preferably in each case independently assumes values of 0, 1 or 2, with the proviso that the sum of the four values of n is at least 1.

The radicals specified for Het in the context of the preceding preferences have already also been listed by way of example in the list given above.

Of particular interest is the use of phthalocyanines of the formula I in which M is twice hydrogen, R are identical —CH$_2$-Het moieties, Het is a γ-butyrolactam, δ-valerolactam or ε-caprolactam radical which is optionally substituted by one or more C$_1$-C$_4$-alkyl groups and is bonded to the CH$_2$ group of the —CH$_2$-Het moiety via the nitrogen atom, and n is in each case independently a value of 0, 1 or 2, with the proviso that the sum of the four values of n is at least 1.

Preference is further given to using phthalocyanines of the formula I in which M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are each identical or different moieties selected from the group consisting of —CH$_2$—N(—X$^1$—R$^1$)(—X$^2$—R$^2$), X$^1$, X$^2$ are each independently a carbonyl group or a chemical single bond, R$^1$ is C$_1$-C$_{15}$-alkyl which is optionally interrupted by from 1 to 4 oxygen atoms in ether function, cyclohexyl which is optionally substituted by one or more C$_1$-C$_{15}$-alkyl groups which are optionally interrupted by from 1 to 4 oxygen atoms in ether function, saturated heterocyclic five- or six-membered radical which is optionally substituted by one or more C$_1$-C$_{15}$-alkyl groups which are optionally interrupted by from 1 to 4 oxygen atoms in ether function, C$_6$-C$_{10}$-aryl which is optionally substituted by one or more C$_1$-C$_{15}$-alkyl which is optionally substituted by from 1 to 4 oxygen atoms in ether function, C$_1$-C$_{15}$-alkoxy, C$_1$-C$_{15}$-alkylamino or C$_1$-C$_{15}$-dialkylamino, heteroaryl having from 3 to 5 carbon atoms which is optionally substituted by one or more C$_1$-C$_{15}$-alkyl which is optionally interrupted by from 1 to 4 oxygen atoms in ether function, C$_1$-C$_{15}$-alkoxy, C$_1$-C$_{15}$-alkylamino or C$_1$-C$_{15}$-dialkylamino, phenyl-C$_1$-C$_4$-alkyl which is optionally substituted in the aryl radical by one or more C$_1$-C$_{15}$-alkyl which is optionally interrupted by from 1 to 4 oxygen atoms in ether function, C$_1$-C$_{15}$-alkoxy, C$_1$-C$_{15}$-alkylamino or C$_1$-C$_{15}$-dialkylamino, or heteroaryl-C$_1$-C$_4$-alkyl having from 3 to 5 carbon atoms in the heteroaryl radical, the latter optionally being substituted by one or more C$_1$-C$_{15}$-alkyl which is optionally interrupted by from 1 to 4 oxygen atoms in ether function, C$_1$-C$_{15}$-alkoxy, C$_1$-C$_{15}$-alkylamino or C$_1$-C$_{15}$-dialkylamino, and R$^2$ is hydrogen or, independently of R$^1$, as defined for R$^1$, and, in the case that X$^2$ is a carbonyl group, R$^2$ is not defined as hydrogen.

Particular preference is given to using phthalocyanines of the formula I in which M is twice hydrogen, R are each identical or different moieties selected from the group consisting of —CH$_2$—N(—X$^1$—R$^1$)(—X$^2$—R$^2$), X$^1$, X$^2$ are each independently a carbonyl group or a chemical single bond, R$^1$ is C$_1$-C$_{15}$-alkyl which is optionally interrupted by from 1 to 4 oxygen atoms in ether function, cyclohexyl which is optionally substituted by one or more C$_1$-C$_{15}$-alkyl groups which are optionally interrupted by from 1 to 4 oxygen atoms in ether function, saturated heterocyclic five- or six-membered radical which is optionally substituted by one or more C$_1$-C$_{15}$-alkyl groups which are optionally interrupted by from 1 to 4 oxygen atoms in ether function, phenyl which is optionally substituted by one or more C$_1$-C$_{15}$-alkyl which is optionally substituted by from 1 to 4 oxygen atoms in ether function, C$_1$-C$_{15}$-alkoxy, C$_1$-C$_{15}$-alkylamino or C$_1$-C$_{15}$-dialkylamino, phenyl-C$_1$-C$_4$-alkyl which is optionally substituted in the aryl radical by one or more C$_1$-C$_{15}$-alkyl which is optionally interrupted by from 1 to 4 oxygen atoms in ether function, C$_1$-C$_{15}$-alkoxy, C$_1$-C$_{15}$-alkylamino or C$_1$-C$_{15}$-dialkylamino, and R$^2$ is hydrogen or, independently of R$^1$, as defined for R$^1$, and, in the case that X$^2$ is a carbonyl group, R$^2$ is not defined as hydrogen.

In the preferences recited above, the variable n preferably in each case independently assumes values of 0, 1 or 2, with the proviso that the sum of the four values of n is at least 1.

The radicals specified for R$^1$ and R$^2$ in the context of the preceding preferences have already also been listed by way of example in the list given above.

Suitable liquids which can be marked in accordance with the invention by means of the phthalocyanines of the formula I described in more detail above and their preferred embodiments are in particular organic liquids, for example alcohols such as methanol, ethanol, propanol, isopropanol, butanol, isobutanol, sec-butanol, pentanol, isopentanol, neopentanol or hexanol, glycols such as 1,2-ethylene glycol, 1,2- or 1,3-propylene glycol, 1,2-, 2,3- or 1,4-butylene glycol, di- or triethylene glycol or di- or tripropylene glycol, ethers such as methyl tert-butyl ether, 1,2-ethylene glycol monomethyl ether or 1,2-ethylene glycol dimethyl ether, 1,2-ethylene glycol monoethyl ether or 1,2-ethylene glycol diethyl ether, 3-methoxypropanol, 3-isopropoxypropanol, tetrahydrofuran or dioxane, ketones such as acetone, methyl ethyl ketone or diacetone alcohol, esters such as methyl acetate, ethyl acetate, propyl acetate or butyl acetate, aliphatic or aromatic hydrocarbons such as pentane, hexane, heptane, octane, isooctane, petroleum ether, toluene, xylene, ethylbenzene, tetralin, decalin, dimethylnaphthalene, white spirit, mineral oil such as benzine, kerosene, diesel oil or heating oil, natural oils such as olive oil, soya oil or sunflower oil, or natural or synthetic engine, hydraulic or gearbox oils, for example motor vehicle engine oils or sewing machine oils, or brake fluids.

Particularly advantageously, the abovementioned phthalocyanines of the formula I and their preferred embodiments are used to mark mineral oils.

The present invention further provides liquids which comprise at least one phthalocyanine of the formula I or a preferred embodiment thereof as a marker.

In particular, mineral oils are claimed which comprise at least one phthalocyanine of the formula I or a preferred embodiment thereof as a marker.

The phthalocyanines of the formula I may also be used as components in additive concentrates (also referred to hereinbelow, following the relevant terminology, as packages) which, in addition to a carrier oil and a mixture of different fuel additives, generally also comprise dyes and also, for invisible fiscal or manufacturer-specific marking, additionally markers. These packages enable the supply of different mineral oil distributors from a pool of unadditized mineral oil, to which the company-specific additization, color and marking are not imparted to the mineral oil until, for example, it is transferred to appropriate transport containers, with the aid of the individual packages.

The components contained in such packages are then in particular:
a) at least one phthalocyanine of the formula I or preferred embodiments thereof,
b) at least one carrier oil,
c) at least one additive selected from the group consisting of detergents, dispersants and valve seat wear-inhibiting additives,
d) and also, if appropriate, further additives and assistants.

The carrier oils used are typically viscous, high-boiling and in particular thermally stable liquids. They cover the hot metal surfaces, for example the intake valves, with a thin liquid film and thus prevent or delay the formation and deposition of decomposition products on the metal surfaces.

Carrier oils useful as component b) of the fuel and lubricant additive concentrates are, for example, mineral carrier oils (base oils), especially those of the Solvent Neutral (SN) 500 to 2000 viscosity class, synthetic carrier oils based on olefin polymers having $M_N$=from 400 to 1800, in particular based on polybutene or polyisobutene (hydrogenated or nonhydrogenated), on poly-alpha-olefins or poly(internal olefins) and also synthetic carrier oils based on alkoxylated long-chain alcohols or phenols. According to the invention, adducts, to be used as carrier oils, of ethylene oxide, propylene oxide and/or butylene oxide to polybutyl alcohols or polyisobutene alcohols are described, for instance, in EP 277 345 A1; further polyalkene alcohol polyalkoxylates to be used in accordance with the invention are described in WO 00/50543 A1. Further carrier oils to be used also include polyalkene alcohol polyether amines, as detailed in WO 00/61708.

It will be appreciated that mixtures of different carrier oils may also be used, as long as they are compatible with one another and with the remaining components of the packages.

Carburetors and intake systems of internal combustion engines, but also injection systems for fuel metering, are being contaminated to an increasing degree by impurities which are caused, for example, by dust particles from the air and uncombusted hydrocarbons from the combustion chamber.

To reduce or prevent these contaminations, additives ("detergents") are added to the fuel to keep valves and carburetors or injection systems clean. Such detergents are generally used in combination with one or more carrier oils. The carrier oils exert an additional "wash function", support and often promote the detergents in their action of cleaning and keeping clean, and can thus contribute to the reduction in the amount of detergents required.

It should also be mentioned here that many of the substances typically used as carrier oils display additional action as detergents and/or dispersants, which is why the proportion of the latter can be reduced in such a case. Such carrier oils having detergent/dispersant action are detailed, for instance, in the last-mentioned WO document.

It is also often impossible to clearly delimit the mode of action of detergents, dispersants and valve seat wear-inhibiting additives, which is why these compounds are listed in summary under component c). Customary detergents which find use in the packages are listed, for example, in WO 00/50543 A1 and WO 00/61708 A1 and include:

polyisobutenamines which are obtainable according to EP-A 244 616 by hydroformylation of highly reactive polyisobutene and subsequent reductive amination with ammonia, monoamines or polyamines, such as dimethylaminopropylamine, ethylenediamine, diethylenetriamine, triethylenetetramine or tetraethylenepentamine, poly(iso)butenamines which are obtainable by chlorination of polybutenes or polyisobutenes having double bonds predominantly in the β- and γ-position and subsequent amination with ammonia, monoamines or the abovementioned polyamines, poly(iso)butenamines which are obtainable by oxidation of double bonds in poly(iso)butenes with air or ozone to give carbonyl or carboxyl compounds and subsequent amination under reducing (hydrogenating) conditions, polyisobutenamines which are obtainable according to DE-A 196 20 262 from polyisobutene epoxides by reaction with amines and subsequent dehydration and reduction of the amino alcohols, polyisobutenamines which optionally contain hydroxyl groups and are obtainable according to WO-A 97/03946 by reaction of polyisobutenes having an average degree of polymerization P of from 5 to 100 with nitrogen oxides or mixtures of nitrogen oxides and oxygen and subsequent hydrogenation of these reaction products, hydroxyl-containing polyisobutenamines which are obtainable according to EP-A 476 485 by reaction of polyisobutene epoxides with ammonia, monoamines or the abovementioned polyamines, polyetheramines which are obtainable by reaction of $C_2$- to $C_{30}$-alkanols, $C_6$- to $C_{30}$-alkanediols, mono- or di-$C_2$- to $C_{30}$-alkylamines, $C_1$- to $C_{30}$-alkylcyclohexanols or $C_1$- to $C_{30}$-alkylphenols with from 1 to 30 mol of ethylene oxide and/or propylene oxide and/or butylene oxide per hydroxyl or amino group and subsequent reductive amination with ammonia, monoamines or the abovementioned polyamines, and also "polyisobutene Mannich bases" which are obtainable according to EP-A 831 141 by reaction of polyisobutene-substituted phenols with aldehydes and monoamines or the abovementioned polyamines.

Further detergents and/or valve seat wear-inhibiting additives to be used are listed, for example, in WO 00/47698 A1 and include compounds which have at least one hydrophobic hydrocarbon radical having a number-average molecular weight ($M_N$) Of from 85 to 20 000 and at least one polar moiety, and which are selected from:

(i) mono- or polyamino groups having up to 6 nitrogen atoms, of which at least one nitrogen atom has basic properties;
(ii) nitro groups, optionally in combination with hydroxyl groups;

(iii) hydroxyl groups in combination with mono- or polyamino groups, in which at least one nitrogen atom has basic properties;
(iv) carboxyl groups or their alkali metal or alkaline earth metal salts;
(v) sulfonic acid groups or their alkali metal or alkaline earth metal salts;
(vi) polyoxy-$C_2$- to -$C_4$-alkylene groups which are terminated by hydroxyl groups, mono- or polyamino groups, in which at least one nitrogen atom has basic properties, or by carbamate groups;
(vii) carboxylic ester groups;
(viii) moieties derived from succinic anhydride and having hydroxyl and/or amino and/or amido and/or imido groups; and
(ix) moieties obtained by Mannich reaction of phenolic hydroxyl groups with aldehydes and mono- or polyamines.

Additives containing mono- or polyamino groups (i) are preferably polyalkenemono- or polyalkenepolyamines based on polypropene or on highly reactive (i.e. having predominantly terminal double bonds, usually in the β- and γ-positions) or conventional (i.e. having predominantly internal double bonds) polybutene or polyisobutene having $M_N$=from 300 to 5000. Such additives based on highly reactive polyisobutene, which can be prepared from the polyisobutene (which may contain up to 20% by weight of n-butene units) by hydroformylation and reductive amination with ammonia, monoamines or polyamines, such as dimethylaminopropylamine, ethylenediamine, diethylenetriamine, triethylenetetramine or tetraethylenepentamine, are disclosed in particular in EP 244 616 A2. When polybutene or polyisobutene having predominantly internal double bonds (usually in the β- and γ-positions) are used as starting materials in the preparation of the additives, a possible preparative route is by chlorination and subsequent amination or by oxidation of the double bond with air or ozone to give the carbonyl or carboxyl compound and subsequent amination under reductive (hydrogenating) conditions. The amines used here for the amination may be the same as those used above for the reductive amination of the hydroformylated highly reactive polyisobutene. Corresponding additives based on polypropene are described in particular in WO 94/24231 A1.

Further preferred additives containing monoamino groups (i) are the hydrogenation products of the reaction products of polyisobutenes having an average degree of polymerization P of from 5 to 100 with nitrogen oxides or mixtures of nitrogen oxides and oxygen, as described in particular in WO 97/03946 A1.

Further preferred additives containing monoamino groups (i) are the compounds obtainable from polyisobutene epoxides by reaction with amines and subsequent dehydration and reduction of the amino alcohols, as described in particular in DE 196 20 262 A1.

Additives containing nitro groups (ii), optionally in combination with hydroxyl groups, are preferably reaction products of polyisobutenes having an average degree of polymerization P of from 5 to 100 or from 10 to 100 with nitrogen oxides or mixtures of nitrogen oxides and oxygen, as described in particular in WO 96/03367 A1 and WO 96/03479 A1. These reaction products are generally mixtures of pure nitropolyisobutanes (e.g. α,β-dinitropolyisobutane) and mixed hydroxynitropolyisobutanes (e.g. α-nitro-β-hydroxypolyisobutane).

Additives containing hydroxyl groups in combination with mono- or polyamino groups (iii) are in particular reaction products of polyisobutene epoxides obtainable from polyisobutene having preferably predominantly terminal double bonds and $M_N$=from 300 to 5000, with ammonia or mono- or polyamines, as described in particular in EP 476 485 A1.

Additives containing carboxyl groups or their alkali metal or alkaline earth metal salts (iv) are preferably copolymers of $C_2$-$C_{40}$-olefins with maleic anhydride which have a total molar mass of from 500 to 20 000 and of whose carboxyl groups some or all have been converted to the alkali metal or alkaline earth metal salts and any remainder of the carboxyl groups has been reacted with alcohols or amines. Such additives are disclosed in particular by EP 307 815 A1. Such additives serve mainly to prevent valve seat wear and can, as described in WO 87/01126 A1, advantageously be used in combination with customary detergents such as poly(iso)butenamines or polyetheramines.

Additives containing sulfonic acid groups or their alkali metal or alkaline earth metal salts (v) are preferably alkali metal or alkaline earth metal salts of an alkyl sulfosuccinate, as described in particular in EP 639 632 A1. Such additives serve mainly to prevent valve seat wear and can be used advantageously in combination with customary detergents such as poly(iso)butenamines or polyetheramines.

Additives containing polyoxy-$C_2$-$C_4$-alkylene moieties (vi) are preferably polyethers or polyetheramines which are obtainable by reaction of $C_2$- to $C_{60}$-alkanols, $C_6$- to $C_{30}$-alkanediols, mono- or di-$C_2$-$C_{30}$-alkylamines, $C_1$-$C_{30}$-alkyl-cyclohexanols or $C_1$-$C_{30}$-alkylphenols with from 1 to 30 mol of ethylene oxide and/or propylene oxide and/or butylene oxide per hydroxyl group or amino group and, in the case of the polyetheramines, by subsequent reductive amination with ammonia, monoamines or polyamines. Such products are described in particular in EP 310 875 A1, EP 356 725 A1, EP 700 985 A1 and U.S. Pat. No. 4,877,416. In the case of polyethers, such products also have carrier oil properties. Typical examples of these are tridecanol butoxylates, isotridecanol butoxylates, isononylphenol butoxylates and polyisobutenol butoxylates and propoxylates and also the corresponding reaction products with ammonia.

Additives containing carboxylic ester groups (vii) are preferably esters of mono-, di- or tricarboxylic acids with long-chain alkanols or polyols, in particular those having a minimum viscosity of 2 $mm^2/s$ at 100° C., as described in particular in DE 38 38 918 A1. The mono-, di- or tricarboxylic acids used may be aliphatic or aromatic acids, and particularly suitable ester alcohols or ester polyols are long-chain representatives having, for example, from 6 to 24 carbon atoms. Typical representatives of the esters are adipates, phthalates, isophthalates, terephthalates and trimellitates of isooctanol, of isononanol, of isodecanol and of isotridecanol. Such products also have carrier oil properties.

Additives containing moieties derived from succinic anhydride and having hydroxyl and/or amino and/or amido and/or imido groups (viii) are preferably corresponding derivatives of polyisobutenylsuccinic anhydride which are obtainable by reacting conventional or highly reactive polyisobutene having $M_N$=from 300 to 5000 with maleic anhydride by a thermal route or via the chlorinated polyisobutene. Particular interest attaches to derivatives with aliphatic polyamines such as ethylenediamine, diethylenetriamine, triethylenetetramine or tetraethylenepentamine. Such gasoline fuel additives are described in particular in U.S. Pat. No. 4,849,572.

Additives containing moieties obtained by Mannich reaction of phenolic hydroxyl groups with aldehydes and mono- or polyamines (ix) are preferably reaction products of polyisobutene-substituted phenols with formaldehyde and mono- or polyamines such as ethylenediamine, diethylenetriamine, triethylenetetramine, tetraethylenepentamine or dimethylaminopropylamine. The polyisobutenyl-substituted phenols may stem from conventional or highly reactive polyisobutene having $M_N$=from 300 to 5000. Such "polyisobutene-Mannich bases" are described in particular in EP 831 141 A1.

For a more precise definition of the additives detailed individually, reference is explicitly made here to the disclosures of the abovementioned prior art documents.

Dispersants as component c) are, for example, imides, amides, esters and ammonium and alkali metal salts of polyisobutenesuccinic anhydrides. These compounds find use especially in lubricant oils, but sometimes also as detergents in fuel compositions.

Further additives and assistants which may, if appropriate, be present as component d) of the packages are organic solvents, for example alcohols such as methanol, ethanol, propanol, isopropanol, butanol, isobutanol, sec-butanol, pentanol, isopentanol, neopentanol or hexanol, for example glycols such as 1,2-ethylene glycol, 1,2- or 1,3-propylene glycol, 1,2-, 2,3- or 1,4-butylene glycol, di- or triethylene glycol or di- or tripropylene glycol, for example ethers such as methyl tert-butyl ether, 1,2-ethylene glycol monomethyl ether or 1,2-ethylene glycol dimethyl ether, 1,2-ethylene glycol monoethyl ether or 1,2-ethylene glycol diethyl ether, 3-methoxypropanol, 3-isopropoxypropanol, tetrahydrofuran or dioxane, for example ketones such as acetone, methyl ethyl ketone or diacetone alcohol, for example esters such as methyl acetate, ethyl acetate, propyl acetate or butyl acetate, for example lactams such as N-methylpyrrolidinone (NMP), for example aliphatic or aromatic hydrocarbons and also mixtures thereof such as pentane, hexane, heptane, octane, isooctane, petroleum ether, toluene, xylene, ethylbenzene, tetralin, decalin, dimethylnaphthalene or white spirit and, for example, mineral oil such as gasoline, kerosene, diesel oil or heating oil, corrosion inhibitors, for example based on ammonium salts, having a tendency to form films, of organic carboxylic acids or of heterocyclic aromatics in the case of ferrous metal corrosion protection, antioxidants or stabilizers, for example based on amines such as p-phenylenediamine, dicyclohexylamine or derivatives thereof or on phenols such as 2,4-di-tert-butylphenol or 3,5-di-tert-butyl-4-hydroxyphenylpropionic acid, demulsifiers, antistats, metallocenes such as ferrocene or methylcyclopentadienylmanganese tricarbonyl, lubricity improvers (lubricity additives) such as certain fatty acids, alkenylsuccinic esters, bis(hydroxyalkyl) fatty amines, hydroxyacetamides or castor oil, amines for reducing the pH of the fuel, further markers other than phthalocyanines of the formula I and their preferred embodiments and dyes.

The concentration of component a), i.e. of the at least one phthalocyanine of the formula I or its preferred embodiments, in the packages is typically selected in such a magnitude that, after addition of the package to the mineral oil, the desired concentration of marker(s) is present therein. Typical concentrations of the markers in the mineral oil are, for instance, in the range from 0.01 up to a few 10 s of ppm by weight.

Component b), i.e. the at least one carrier oil, is present in the packages typically in a concentration of from 1 to 50% by weight, in particular from 5 to 30% by weight, and component c), i.e. the at least one detergent and/or the at least one dispersant, typically in a concentration of from 25 to 90% by weight, in particular from 30 to 80% by weight, based in each case on the total amount of components a) to c) and, where present, d), the sum of the individual concentrations of components a) to c) and, where present, d) adding up to 100% by weight.

When, as component d), corrosion inhibitors, antioxidants or stabilizers, demulsifiers, antistats, metallocenes, lubricity improvers and amines to reduce the pH of the fuel are present in the packages, the sum of their concentrations typically does not exceed 10% by weight, based on the total weight of the package (i.e. the total amount of components a) to c) and d)), the concentration of the corrosion inhibitors and demulsifiers being typically in the range of from in each case about 0.01 to 0.5% by weight of the total amount of the package.

When, as component d), additional organic solvents (i.e. not already introduced with the remaining components) are present in the packages, the sum of their concentrations typically does not exceed 20% by weight, based on the total amount of the package. These solvents generally stem from solutions of the markers and/or dyes, which are added to the packages instead of the pure markers and/or dyes with a view to more precise meterability.

When, as component d), further markers other than phthalocyanines of the formula I or their preferred embodiments are present in the packages, their concentration is in turn based on the content that they are to have after addition of the packages in mineral oil. That which was stated for component a) applies mutatis mutandis.

When, as component d), dyes are present in the packages, their concentration is typically, for instance, between 0.1 to 5% by weight, based on the total amount of the package.

Additionally claimed in the context of the present invention are phthalocyanines of the formula Ia

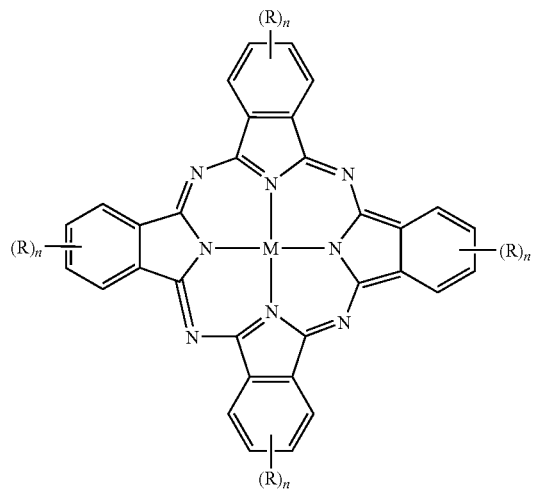

(Ia)

in which M is twice hydrogen, twice lithium, magnesium, zinc, copper, nickel, VO, TiO, AlCl, AlOCOCH$_3$, AlO-COCF$_3$, SiCl$_2$ or Si(OH)$_2$, R are each identical or different —CH$_2$-Het moieties, Het is a saturated heterocyclic five-, six- or seven-membered radical which is optionally substituted by one or more C$_1$-C$_{20}$-alkyl groups which are optionally interrupted by from 1 to 4 oxygen atoms in ether function, and in which one CH$_2$ group is optionally replaced by a carbonyl group, the saturated heterocyclic radical being bonded to the CH$_2$ group of the —CH$_2$-Het moiety either via a suitable heteroatom or a carbon atom. The variable n in each case independently assumes values of 0, 1, 2, 3 or 4, with the proviso that the sum of the four values of n is at least 1.

In the preferred phthalocyanines of the formula I, M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are each identical or different —CH$_2$-Het moieties, Het is a saturated heterocyclic five-, six- or seven-membered radical which is optionally substituted by one or more C$_1$-C$_{15}$-alkyl groups which are optionally interrupted by from 1 to 4 oxygen atoms in ether function, and in which one CH$_2$ group is optionally replaced by a carbonyl group.

Particularly preferred phthalocyanines are those in which, in formula Ia, M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are identical or different —CH$_2$-Het moieties, Het is a saturated heterocyclic five-, six- or seven-membered radical which is optionally substituted by one or more C$_1$-C$_4$-alkyl groups and in which one CH$_2$ group is optionally replaced by a carbonyl group.

Of particular interest are phthalocyanines in which, in formula Ia, M is twice hydrogen, R are identical or different —CH$_2$-Het moieties, Het is a saturated heterocyclic five-, six- or seven-membered radical which is optionally substituted by one or more C$_1$-C$_4$-alkyl groups and in which the CH$_2$ group adjacent to the nitrogen atom is optionally replaced by a carbonyl group.

In the preferences recited above, the saturated heterocyclic radical in the phthalocyanines of the formula Ia is bonded to the CH$_2$ group of the —CH$_2$-Het moiety either via a suitable nitrogen atom or a carbon atom; in addition, in formula Ia, the variable n preferably in each case independently assumes values of 0, 1 or 2, with the proviso that the sum of the four values of n is at least 1.

Of very particular interest are phthalocyanines in which, in formula Ia, M is twice hydrogen, R are identical —CH$_2$-Het moieties, Het is a γ-butyrolactam, δ-valerolactam or ε-caprolactam radical which is optionally substituted by one or more C$_1$-C$_4$-alkyl groups and is bonded to the CH$_2$ group of the —CH$_2$-Het moiety via the nitrogen atom, and n is in each case independently a value of 0, 1 or 2, with the proviso that the sum of the four values of n is at least 1.

It should be made clear here that the values of the variables n each relate to an individual molecule of the compounds of the formulae I and Ia described above and are thus inevitably integers. However, where an ensemble of molecules is considered, as is typically obtained as a result of the synthesis, there will of course be, from a statistical point of view, rational numerical values for the average number of R radicals bonded to each benzene ring of the basic phthalocyanine structure.

The phthalocyanines of the formulae I and Ia may be obtained from the unsubstituted phthalocyanines by reacting with the corresponding hydroxymethylated compounds in a concentrated acid (method A), in which case the hydroxymethylated compounds are obtainable by methods commonly known to those skilled in the art. The preparation of hydroxymethyllactams from the lactams is described, for example, in the documents U.S. Pat. Nos. 4,769,454 und 3,073,843.

Moreover, the phthalocyanines of the formulae I and Ia may also be reacted with nitrogen compounds such as amides, lactams, imidazoles, etc., and paraformaldehyde in the presence of acid to give the desired markers (method B).

The reaction conditions (temperature, reaction time, concentration, excess of the hydroxymethyl compound, etc.) allows the degree of substitution of the phthalocyanine and thus its solubility to be controlled. The degree of substitution can be determined, for example, by mass spectrometry.

Phthalocyanine 1:

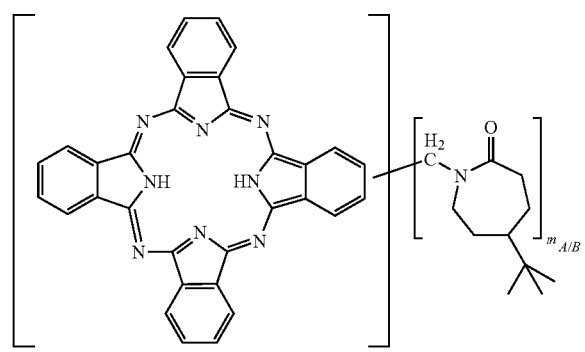

The compound was prepared by both methods A and B:

Method A:

100 g of polyphosphoric acid were initially charged at from 40 to 45° C., 5.14 g (0.010 mol) of metal-free phthalocyanine were introduced within 20 minutes, the mixture was stirred for a further 30 minutes and 8.0 g (0.040 mol) of 4-tert-butyl-N-hydroxymethylcaprolactam were added within 20 minutes. The mixture was stirred at 105° C. for a further 8 hours and then left to cool to 50° C., before it was diluted with 500 g of ice-water and subsequently filtered with suction. The moist residue was taken up in 600 ml of water and adjusted to a pH of 12.5 using concentrated sodium hydroxide solution. The mixture was stirred for a further 2 hours, filtered and dried under reduced pressure. The yield was 7 g. The average value for $m_A$ in the formula shown above was from 3 to 4.

Method B:

100 g of polyphosphoric acid were initially charged at from 40 to 45° C. and 5.14 g (0.010 mol) of metal-free phthalocyanine and 2.2 g (0.075 mol) of paraformaldehyde were introduced within 20 minutes. The mixture was then left to stir at 50° C. for a further 4 hours and 12.7 g (0.075 mol) of 4-tert-butylcaprolactam were added. The mixture was stirred at 105° C. for a further 7.5 hours and then left to cool to 50° C., before it was diluted with 500 g of ice-water and subsequently filtered with suction. The moist residue was taken up in 600 ml of water and adjusted to a pH of 12.5 using concentrated sodium hydroxide solution. The mixture was stirred for a further 2 hours, filtered and dried under reduced pressure. The yield was 10 g. The average value of $m_B$ in the formula shown above was about 4.

In a similar manner, the phthalocyanines 2 to 5 shown below were prepared:

Phthalocyanine 2 (Prepared by Method A ($m_A$ from 3 to 4) and B ($m_B$ Approx. 4)):

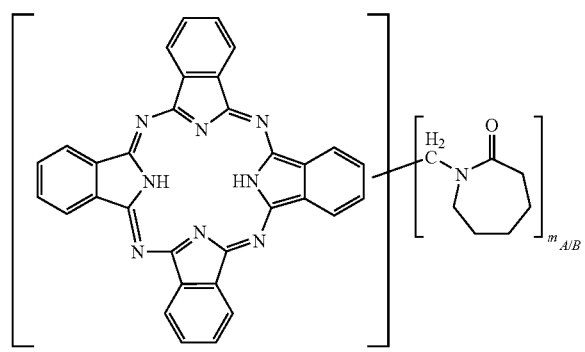

Phthalocyanine 3 (Prepared by Method B ($m_B$ Approx. 4)):

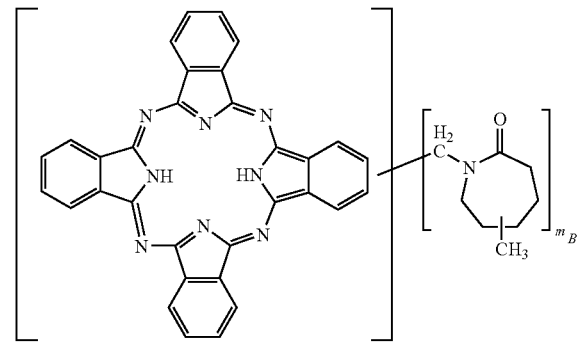

Phthalocyanine 4 (Prepared by Method B ($m_B$ Approx. 4)):

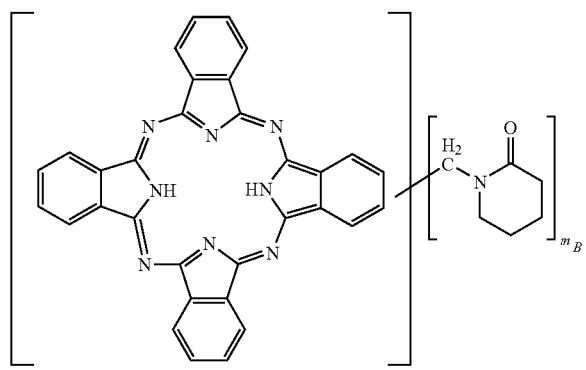

Phthalocyanine 5 (Prepared by Method B ($m_B$ Approx. 4)):

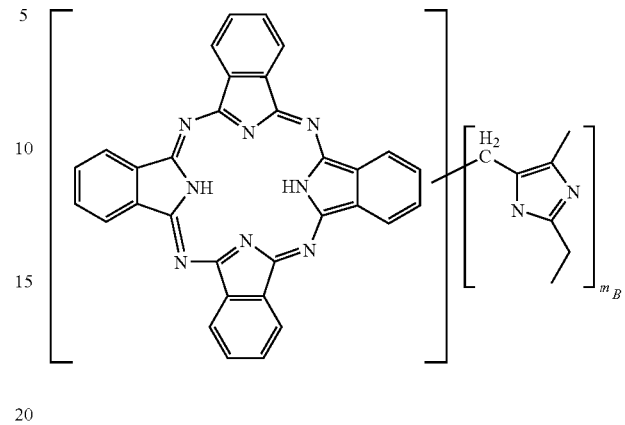

Phthalocyanine 6 (Comparison; Prepared According to Example 1 of WO 98/52950 A1):

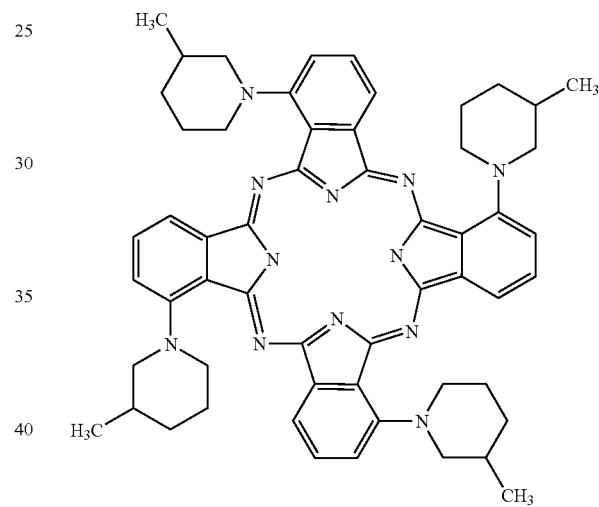

Long-Term Stability:

The long-term stability of the phthalocyanines 1 and 2 and of the phthalocyanine 6 (comparison) was investigated in the presence of a commercial detergent for mineral oil fuels (polyisobutenamine (PIBA); solution having a PIBA content of 50% by weight). For this purpose, from 50 to 100 mg of the particular compound were dissolved in 50 ml of Shellsol AB or, when the solubility of the compound in Shellsol AB was insufficient, it was first incipiently dissolved with approx. 5 ml of isopropanol or N-methylpyrrolidone and then made up to 50 ml using Shellsol AB. Subsequently, the solution was filtered through a fluted paper filter.

From 1 to 3 mol of the filtrate were made up to 10 ml with detergent (corresponding to a concentration of the particular compound of from 0.01 to 0.08%) and analyzed in 1 mm cuvettes against the corresponding unadditized reference.

The samples were transferred to 10 ml ampoules, sealed in an airtight manner and stored at 50° C. in a waterbath.

The experiments are reproduced in the table which follows. All measurements were normalized to the starting extinction.

Comparison of the long-term stability at 50° C. compared to the detergent

| Phthalocyanine | Storage time (h) | Absorption maximum (nm) | Extinction (normalized) |
|---|---|---|---|
| 6 (comparison) | 0 | 768 | 1.00 |
| | 114 | | 0.33 |
| | 161 | | 0.20 |
| | 283 | | 0.05 |
| 1 | 0 | 599 | 1.00 |
| | 16 | | 0.98 |
| | 163 | | 0.97 |
| | 474 | | 0.95 |
| | 524 | | 0.93 |
| 2 | 0 | 695 | 1.00 |
| | 114 | | 0.89 |
| | 161 | | 0.88 |
| | 283 | | 0.78 |
| | 474 | | 0.77 |
| | 668 | | 0.81 |

While, in the case of the phthalocyanine 6 (comparison), the normalized extinction had fallen to 5% of original value after 283 hours, the values for the phthalocyanines 1 and 2, after distinctly longer storage times of 524 and 668 hours respectively, still amounted to 93 and 81%, respectively, of the original values.

What is claimed is:

1. A phthalocyanine of the formula Ia

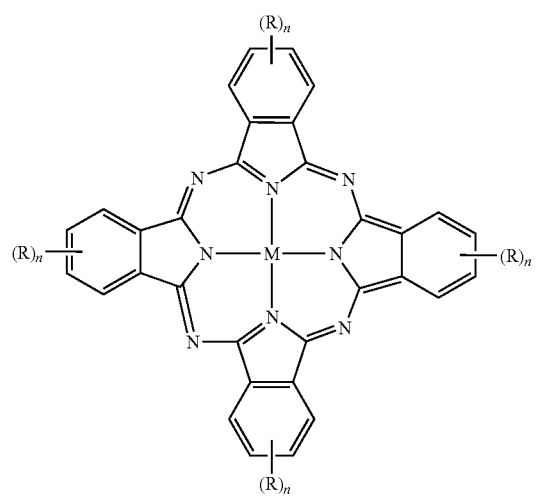

(Ia)

where, in formula Ia,

M is twice hydrogen,

R are identical or different —CH$_2$-Het moieties,

Het is a saturated nitrogen-containing heterocyclic five-, six- or seven-membered radical which is optionally substituted by one or more C$_1$-C$_4$-alkyl groups and in which the CH$_2$ group adjacent to the nitrogen atom is optionally replaced by a carbonyl group, the saturated heterocyclic radical being bonded to the CH$_2$ group of the —CH$_2$-Het moiety either via a suitable heteroatom or a carbon atom, and n is in each case independently a value of 0, 1 or 2, with the proviso that the sum of the four values of n is at least 1.

2. A phthalocyanine according to claim 1, where, in formula Ia,

M is twice hydrogen,

R are identical —CH$_2$-Het moieties,

Het is a γ-butyrolactam, δ-valerolactam or ε-caprolactam radical which is optionally substituted by one or more C$_1$-C$_4$-alkyl groups and is bonded to the CH$_2$ group of the —CH$_2$-Het moiety via nitrogen atom, and n is in each case independently a value of 0, 1 or 2, with the proviso that the sum of the four values of n is at least 1.

3. A marker comprising a mineral oil and at least one phthalocyanine of the formula I

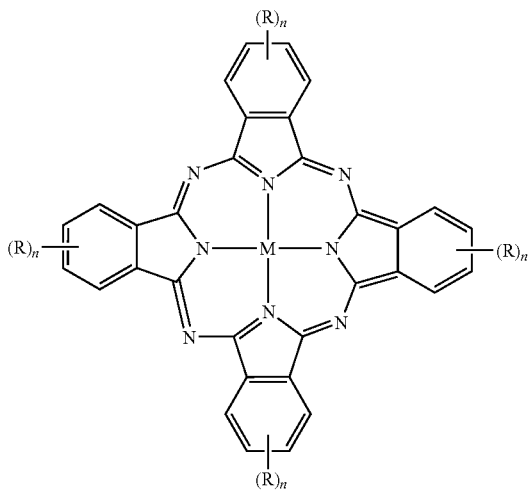

(I)

where, in formula I,

M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are each identical or different moieties selected from the group consisting of —CH$_2$—N(—X$^1$—R$^1$)(—X$^2$—R$^2$) and —CH$_2$-Het, X$^1$, X$^2$ are each independently a carbonyl group or a chemical single bond, R$^1$ is C$_1$-C$_{20}$-alkyl which is optionally interrupted by from 1 to 4 oxygen atoms in ether function, C$_5$-C$_7$-cycloalkyl which is optionally substituted by one or more C$_1$-C$_{20}$-alkyl groups which are optionally interrupted by from 1 to 4 oxygen atoms in ether function, saturated heterocyclic five- or six-membered radical which is optionally substituted by one or more C$_1$-C$_{20}$-alkyl groups which are optionally interrupted by from 1 to 4 oxygen atoms in ether function, C$_6$-C$_{10}$-aryl which is optionally substituted by one or more halogen, cyano, nitro, hydroxyl, amino, C$_1$-C$_{20}$-alkyl which is optionally substituted by from 1 to 4 oxygen atoms in ether function, C$_1$-C$_{20}$-alkoxy, C$_1$-C$_{20}$-alkylamino or C$_1$-C$_{20}$-dialkylamino, heteroaryl having from 3 to 12 carbon atoms which is optionally substituted by one or more C$_1$-C$_{20}$-alkyl which is optionally interrupted by from 1 to 4 oxygen atoms in ether function, C$_1$-C$_{20}$-alkoxy, C$_1$-C$_{20}$alkylamino or C$_1$-C$_{20}$-dialkylamino, C$_6$-C$_{10}$-aryl-C$_1$-C$_4$-alkyl which is optionally substituted in the aryl radical by one or more halogen, cyano, nitro, hydroxyl, amino, C$_1$-C$_{20}$-alkyl which is optionally interrupted by from 1 to 4 oxygen atoms in ether function, $C_1$-$C_{20}$-alkoxy, $C_1$-$C_{20}$-alkylamino or $C_1$-$C_{20}$-dialkylamino, or heteroaryl-$C_1$-$C_4$-alkyl having from 3 to 12 carbon atoms in the heteroaryl radical, the latter optionally being substituted by one or more $C_1$-$C_{20}$-alkyl which is optionally interrupted by from 1 to 4 oxygen atoms in ether function, $C_1$-$C_{20}$-alkoxy, $C_1$-$C_{20}$-alkylamino or $C_1$-$C_{20}$-dialkylamino, $R^2$ is hydrogen or, independently of $R^1$, as defined for $R^1$, and, in the case that $X^2$ is a carbonyl group, $R^2$ is not defined as hydrogen, Het is a saturated heterocyclic five-, six- or seven-membered radical which is optionally substituted by one or more $C_1$-$C_{20}$-alkyl groups which is optionally interrupted by from 1 to 4 oxygen atoms in ether function, and in which one $CH_2$ group is optionally replaced by a carbonyl group, or heteroaryl having from 3 to 12 carbon atoms which is optionally substituted by one or more $C_1$-$C_{20}$-alkyl groups which are optionally interrupted by from 1 to 4 oxygen atoms in ether function, the saturated heterocyclic radical or the heteroaryl being bonded to the $CH_2$ group of the —$CH_2$-Het moiety either via a suitable heteroatom or a carbon atom, and n is in each case independently a value of 0, 1, 2, 3 or 4, with the proviso that the sum of the four values of n is at least 1.

4. The marker according to claim 3, wherein, in formula I,

M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are each identical or different —$CH_2$-Het moieties, Het is a saturated heterocyclic five-, six- or seven-membered ring which is optionally substituted by one or more $C_1$-$C_{15}$-alkyl groups which are optionally interrupted by from 1 to 4 oxygen atoms in ether function, and in which one $CH_2$ group is optionally replaced by a carbonyl group, or heteroaryl having from 3 to 5 carbon atoms which is optionally substituted by one or more $C_1$-$C_{15}$-alkyl groups which are optionally interrupted by from 1 to 4 oxygen atoms in ether function, the saturated heterocyclic radical or the heteroaryl being bonded to the $CH_2$ group of the —$CH_2$-Het moiety either via a suitable heteroatom or a carbon atom, and n in each case independently has a value of 0, 1 or 2, with the proviso that the sum of the four values of n is at least 1.

5. The marker according to claim 3, wherein, in formula I,

M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are identical or different —$CH_2$-Het moieties, Het is a saturated heterocyclic five-, six- or seven-membered radical which is optionally substituted by one or more $C_1$-$C_4$-alkyl groups and in which one $CH_2$ group is optionally replaced by a carbonyl group, or heteroaryl having from 3 to 5 carbon atoms which is optionally substituted by one or more $C_1$-$C_4$-alkyl groups, the saturated heterocyclic radical or the heteroaryl being bonded to the $CH_2$ group of the —$CH_2$-Het moiety either via a suitable heteroatom or a carbon atom, and n is in each case independently a value of 0, 1 or 2, with the proviso that the sum of the four values of n is at least 1.

6. The marker according to claim 3, wherein, in formula I,

M is twice hydrogen,

R are identical or different —$CH_2$-Het moieties, Het is a saturated, nitrogen-containing, five-, six- or seven-membered radical which is optionally substituted by one or more $C_1$-$C_4$-alkyl groups and in which the $CH_2$ group adjacent to the nitrogen atom is replaced by a carbonyl group, or nitrogen-containing heteroaryl having from 3 to 5 carbon atoms which is optionally substituted by one or more $C_1$-$C_4$-alkyl groups, the saturated heterocyclic radical or the heteroaryl being bonded to the $CH_2$ group of the —$CH_2$-Het moiety either via a suitable nitrogen atom or a carbon atom, and n is in each case independently a value of 0, 1 or 2, with the proviso that the sum of the four values of n is at least 1.

7. The marker according to claim 3, wherein, in formula I,

M is twice hydrogen,

R are identical —$CH_2$-Het moieties,

Het is a γ-butyrolactam, δ-valerolactam or ε-caprolactam radical which is optionally substituted by one or more $C_1$-$C_4$-alkyl groups and is bonded to the $CH_2$ group of the —$CH_2$-Het moiety via the nitrogen atom, and n is in each case independently a value of 0, 1 or 2, with the proviso that the sum of the four values of n is at least 1.

8. The marker according to claim 3, wherein, in formula I,

M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are each identical or different moieties selected from the group consisting of —$CH_2$—N(—$X^1$—$R^1$)(—$X^2$—$R^2$), $X^1$, $X^2$ are each independently a carbonyl group or a chemical single bond, $R^1$ is $C_1$-$C_{15}$-alkyl which is optionally interrupted by from 1 to 4 oxygen atoms in ether function, cyclohexyl which is optionally substituted by one or more $C_1$-$C_{15}$-alkyl groups which are optionally interrupted by from 1 to 4 oxygen atoms in ether function, saturated heterocyclic five- or six-membered radical which is optionally substituted by one or more $C_1$-$C_{15}$-alkyl groups which are optionally interrupted by from 1 to 4 oxygen atoms in ether function, $C_6$-$C_{10}$-acyl which is optionally substituted by one or more $C_1$-$C_{15}$-alkyl which is optionally substituted by from 1 to 4 oxygen atoms in ether function, $C_1$-$C_{15}$-alkoxy, $C_1$-$C_{15}$-alkylamino or $C_1$-$C_{15}$-dialkylamino, heteroaryl having from 3 to 5 carbon atoms which is optionally substituted by one or more $C_1$-$C_{15}$-alkyl which is optionally interrupted by from 1 to 4 oxygen atoms in ether function, $C_1$-$C_{15}$-alkoxy, $C_1$-$C_{15}$-alkylamino or $C_1$-$C_{15}$-dialkylamino, phenyl-$C_1$-$C_4$-alkyl which is optionally substituted in the aryl radical by one or more $C_1$-$C_{15}$-alkyl which is optionally interrupted by from 1 to 4 oxygen atoms in ether function, $C_1$-$C_{15}$-alkoxy, $C_1$-$C_{15}$-alkylamino or $C_1$-$C_{15}$-dialkylamino, or heteroaryl-$C_1$-$C_4$-alkyl having from 3 to 5 carbon atoms in the heteroaryl radical, the latter optionally being substituted by one or more $C_1$-$C_{15}$-alkyl which is optionally interrupted by from 1 to 4 oxygen atoms in ether function, $C_1$-$C_{15}$-alkoxy, $C_1$-$C_{15}$-alkylamino or $C_1$-$C_{15}$-dialkylamino, $R^2$ is hydrogen or, independently of $R^1$, as defined for $R^1$, and, in the case that $X^2$ is a carbonyl group, $R^2$ is not defined as hydrogen, and n is in each case independently a value of 0, 1 or 2, with the proviso that the sum of the four values of n is at least 1.

9. The marker according to claim 3, wherein, in formula I,

M is twice hydrogen,

R are each identical or different moieties selected from the group consisting of —$CH_2$—N(—$X^1$—$R^1$)(—$X^2$—$R^2$), $X^1$, $X^2$ are each independently a carbonyl group or a chemical single bond, $R^1$ is $C_1$-$C_{15}$-alkyl which is optionally interrupted by from 1 to 4 oxygen atoms in ether function, cyclohexyl which is optionally substituted by one or more $C_1$-$C_{15}$-alkyl groups which are optionally interrupted by from 1 to 4 oxygen atoms in ether function, saturated heterocyclic five- or six-membered radical which is optionally substituted by one or more $C_1$-$C_{15}$-alkyl groups which are optionally interrupted by from 1 to 4 oxygen atoms in ether function, phenyl which is optionally substituted by one or more $C_1$-$C_{15}$-alkyl which is optionally interrupted by from 1 to 4 oxygen atoms in ether function, $C_1$-$C_{15}$-alkoxy, $C_1$-$C_{15}$-alkylamino or $C_1$-$C_{15}$-dialkylamino, or phenyl-$C_1$-$C_4$-alkyl which is optionally substituted in the aryl radical by one or more $C_1$-$C_{15}$-alkyl which is optionally interrupted by from 1 to 4 oxygen atoms in ether function, $C_1$-$C_{15}$-alkoxy, $C_1$-$C_{15}$-alkylamino or $C_1$-$C_{15}$-dialkylamino, $R^2$ is hydrogen or, independently of $R^1$, as defined for $R^1$, and, in the case that $X^2$ is a carbonyl group, $R^2$ is not defined as hydrogen, and n is in each case independently a value of 0, 1 or 2, with the proviso that the sum of the four values of n is at least 1.

10. A method for marking a liquid, said method comprising adding to said liquid a phthalocyanine of the formula I

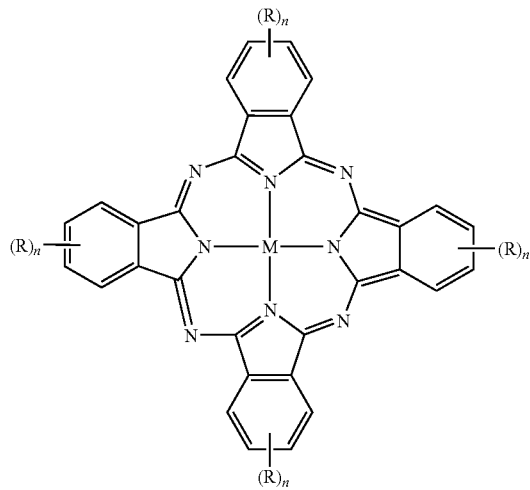

(I)

where, in formula I,

M is twice hydrogen, twice lithium, magnesium, zinc, copper, nickel, VO, TiO, AlCl, $AlOCOCH_3$, $AlOCOCF_3$, $SiCl_2$ or $Si(OH)_2$, R are each identical or different moieties selected from the group consisting of —$CH_2$—N(—$X^1$—$R^1$)(—$X^2R^2$) and —$CH_2$-Het, $X^1$, $X^2$ are each independently a carbonyl group or a chemical single bond, $R^1$ is $C_1$-$C_{20}$-alkyl which is optionally interrupted by from 1 to 4 oxygen atoms in ether function, $C_5$-$C_7$-cycloalkyl which is optionally substituted by one or more $C_1$-$C_{20}$-alkyl groups which are optionally interrupted by from 1 to 4 oxygen atoms in ether function, saturated heterocyclic five- or six-membered radical which is optionally substituted by one or more $C_1$-$C_{20}$-alkyl groups which are optionally interrupted by from 1 to 4 oxygen atoms in ether function, $C_6$-$C_{10}$-aryl which is optionally substituted by one or more halogen, cyano, nitro, hydroxyl, amino, $C_1$-$C_{20}$-alkyl which is optionally substituted by from 1 to 4 oxygen atoms in ether function, $C_1$-$C_{20}$-alkoxy, $C_1$-$C_{20}$-alkylamino or $C_1$-$C_{20}$dialkylamino, heteroaryl having from 3 to 12 carbon atoms which is optionally substituted by one or more $C_1$-$C_{20}$-alkyl which is optionally interrupted by from 1 to 4 oxygen atoms in ether function, $C_1$-$C_{20}$-alkoxy, $C_1$-$C_{20}$-alkylamino or $C_1$-$C_{20}$-dialkylamino, $C_6$-$C_{10}$-aryl-$C_1$-$C_4$-alkyl which is optionally substituted in the aryl radical by one or more halogen, cyano, nitro, hydroxyl, amino, $C_1$-$C_{20}$-alkyl which is optionally interrupted by from 1 to 4 oxygen atoms in ether function, $C_1$-$C_{20}$-alkoxy, $C_1$-$C_{20}$-alkylamino or $C_1$-$C_{20}$-dialkylamino, or heteroaryl-$C_1$-$C_4$-alkyl having from 3 to 12 carbon atoms in the heteroaryl radical, the latter optionally being substituted by one or more $C_1$-$C_{20}$-alkyl which is optionally interrupted by from 1 to 4 oxygen atoms in ether function, $C_1$-$C_{20}$-alkoxy, $C_1$-$C_{20}$-alkylamino or $C_1$-$C_{20}$-dialkylamino, $R^2$ is hydrogen or, independently of $R^1$, as defined for $R^1$, and, in the case that $X^2$ is a carbonyl group, $R^2$ is not defined as hydrogen, Het is a saturated heterocyclic five-, six- or seven-membered radical which is optionally substituted by one or more $C_1$-$C_{20}$-alkyl groups which is optionally interrupted by from 1 to 4 oxygen atoms in ether function, and in which one $CH_2$ group is optionally replaced by a carbonyl group, or heteroaryl having from 3 to 12 carbon atoms which is optionally substituted by one or more $C_1$-$C_{20}$-alkyl groups which are optionally interrupted by from 1 to 4 oxygen atoms in ether function, the saturated heterocyclic radical or the heteroaryl being bonded to the $CH_2$ group of the —$CH_2$-Het moiety either via a suitable heteroatom or a carbon atom, and n is in each case independently a value of 0, 1, 2, 3 or 4, with the proviso that the sum of the four values of n is at least 1.

11. The method according to claim 10, wherein, in formula I,

M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are each identical or different —CH$_2$-Het moieties, Het is a saturated heterocyclic five-, six- or seven-membered ring which is optionally substituted by one or more C$_1$-C$_{15}$-alkyl groups which are optionally interrupted by from 1 to 4 oxygen atoms in ether function, and in which one CH$_2$ group is optionally replaced by a carbonyl group, or heteroaryl having from 3 to 5 carbon atoms which is optionally substituted by one or more C$_1$-C$_{15}$-alkyl groups which are optionally interrupted by from 1 to 4 oxygen atoms in ether function, the saturated heterocyclic radical or the heteroaryl being bonded to the CH$_2$ group of the —CH$_2$-Het moiety either via a suitable heteroatom or a carbon atom, and n i a each case independently has a value of 0, 1 or 2, with the proviso that the sum of the four values of n is at least 1.

12. The method according to claim 10, wherein, in formula I,

M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are identical or different —CH$_2$-Het moieties, Het is a saturated heterocyclic five-, six- or seven-membered radical which is optionally substituted by one or more C$_1$-C$_4$-alkyl groups and in which one CH$_2$ group is optionally replaced by a carbonyl group, or heteroaryl having from 3 to 5 carbon atoms which is optionally substituted by one or more C$_1$-C$_4$-alkyl groups, the saturated heterocyclic radical or the heteroaryl being bonded to the CH$_2$ group of the —CH$_2$-Het moiety either via a suitable heteroatom or a carbon atom, and n is in each case independently a value of 0, 1 or 2, with the proviso that the sum of the four values of n is at least 1.

13. The method according to claim 10, wherein, in formula I,

M is twice hydrogen,

R are identical or different —CH$_2$-Het moieties,

Het is a saturated, nitrogen-containing, five-, six- or seven-membered radical which is optionally substituted by one or more C$_1$-C$_4$-alkyl groups and in which the CH$_2$ group adjacent to the nitrogen atom is replaced by a carbonyl group, or nitrogen-containing heteroaryl having from 3 to 5 carbon atoms which is optionally substituted by one or more C$_1$-C$_4$-alkyl groups, the saturated heterocyclic radical or the heteroaryl being bonded to the CH$_2$ group of the —CH$_2$-Het moiety either via a suitable nitrogen atom or a carbon atom, and n is in each case independently a value of 0, 1 or 2, with the proviso that the sum of the four values of n is at least 1.

14. The method according to claim 10, wherein, in formula I,

M is twice hydrogen,

R are identical —CH$_2$-Het moieties,

Het is a γ-butyrolactam, δ-valerolactam or ε-caprolactam radical which is optionally substituted by one or more C$_1$-C$_4$-alkyl groups and is bonded to the CH$_2$ group of the —CH$_2$-Het moiety via the nitrogen atom, and n is in each case independently a value of 0, 1 or 2, with the proviso that the sum of the four values of n is at least 1.

15. The method according to claim 10, wherein, in formula I,

M is twice hydrogen, twice lithium, magnesium, zinc, copper, nickel, VO, TiO, AlCl, AlOCOCH$_3$, AlOCOCF$_3$, SiCl$_2$ or Si(OH)$_2$, R are each identical or different moieties selected from the group consisting of —CH$_2$—N(—X$^1$—R$^1$)(—X$^2$—R$^2$), X$^1$, X$^2$ are each independently a carbonyl group or a chemical single bond, R$^1$ is C$_1$-C$_{15}$-alkyl which is optionally interrupted by from 1 to 4 oxygen atoms in ether function, cyclohexyl which is optionally substituted by one or more C$_1$-C$_{15}$-alkyl groups which are optionally interrupted by from 1 to 4 oxygen atoms in ether function, saturated heterocyclic five- or six-membered radical which is optionally substituted by one or more C$_1$-C$_{15}$-alkyl groups which are optionally interrupted by from 1 to 4 oxygen atoms in ether function, C$_6$-C$_{10}$-aryl which is optionally substituted by one or more C$_1$-C$_{15}$-alkyl which is optionally substituted by from 1 to 4 oxygen atoms in ether function, C$_1$-C$_{15}$-alkoxy, C$_1$-C$_{15}$-alkylamino or C$_1$-C$_{15}$-dialkylamino, heteroaryl having from 3 to 5 carbon atoms which is optionally substituted by one or more C$_1$-C$_{15}$-alkyl which is optionally interrupted by from 1 to 4 oxygen atoms in ether function, C$_1$-C$_{15}$-alkoxy, C$_1$-C$_{15}$-alkylamino or C$_1$-C$_{15}$-dialkylamino, phenyl-C$_1$-C$_4$-alkyl which is optionally substituted in the aryl radical by one or more C$_1$-C$_{15}$-alkyl which is optionally interrupted by from 1 to 4 oxygen atoms in ether function, C$_1$-C$_{15}$-alkoxy, C$_1$-C$_{15}$-alkylamino or C$_1$-C$_{15}$-dialkylamino, or heteroaryl-C$_1$-C$_4$-alkyl having from 3 to 5 carbon atoms in the heteroaryl radical, the latter optionally being substituted by one or more C$_1$-C$_{15}$-alkyl which is optionally interrupted by from 1 to 4 oxygen atoms in ether function, C$_1$-C$_{15}$-alkoxy, C$_1$-C$_{15}$-alkylamino or C$_1$-C$_{15}$-dialkylamino, R$^2$ is hydrogen or, independently of R$^1$, as defined for R$^1$, and, in the case that X$^2$ is a carbonyl group, R$^2$ is not defined as hydrogen, and n is in each case independently a value of 0, 1 or 2, with the proviso that the sum of the four values of n is at least 1.

16. The method according to claim 10, wherein, in formula I,

M is twice hydrogen,

R are each identical or different moieties selected from the group consisting of —CH$_2$—N(—X$^1$—R$^1$) (—X$^2$—R$^2$), X$^1$, X$^2$ are each independently a carbonyl group or a chemical single bond, R$^1$ is C$_1$-C$_{15}$-alkyl which is optionally interrupted by from 1 to 4 oxygen atoms in ether function, cyclohexyl which is optionally substituted by one or more C$_1$-C$_{15}$-alkyl groups which are optionally interrupted by from 1 to 4 oxygen atoms in ether function, saturated heterocyclic five- or six-membered radical which is optionally substituted by one or more $C_1$-$C_{15}$-alkyl groups which are optionally interrupted by from 1 to 4 oxygen atoms in ether function, phenyl which is optionally substituted by one or more $C_1$-$C_{15}$-alkyl which is optionally substituted by from 1 to 4 oxygen atoms in ether function, $C_1$-$C_{15}$-alkoxy, $C_1$-$C_{15}$-alkylamino or $C_1$-$C_{15}$-dialkylamino, or phenyl-$C_1$-$C_4$-alkyl which is optionally substituted in the aryl radical by one or more $C_1$-$C_{15}$-alkyl which is optionally interrupted by from 1 to 4 oxygen atoms in ether function, $C_1$-$C_{15}$-alkoxy, $C_1$-$C_{15}$-alkylamino or $C_1$-$C_{15}$-dialkylamino, $R^2$ is hydrogen or, independently of $R^1$, as defined for $R^1$, and, in the case that $X^2$ is a carbonyl group, $R^2$ is not defined as hydrogen, and n is in each case independently a value of 0, 1 or 2, with the proviso that the sum of the four values of n is at least 1.

17. The method according to any one of claims 10-16, wherein the liquid is a mineral oil.

* * * * *